(12) United States Patent
Moghadam

(10) Patent No.: US 11,324,562 B2
(45) Date of Patent: May 10, 2022

(54) LATEX GLOVE INFLATION ASSEMBLY

(71) Applicant: Majid Moghadam, Downey, CA (US)

(72) Inventor: Majid Moghadam, Downey, CA (US)

( * ) Notice: Subject to any disclaimer, the term of this patent is extended or adjusted under 35 U.S.C. 154(b) by 273 days.

(21) Appl. No.: 16/582,856

(22) Filed: Sep. 25, 2019

(65) Prior Publication Data

US 2021/0085412 A1 Mar. 25, 2021

(51) Int. Cl.
*A61B 42/50* (2016.01)
*A47G 25/90* (2006.01)

(52) U.S. Cl.
CPC ............ *A61B 42/50* (2016.02); *A47G 25/904* (2013.01)

(58) Field of Classification Search
CPC ...... A47G 25/904; A47G 25/90; A41D 19/00; A41D 19/0034; A41D 19/015; A41D 19/0044; A41D 19/0048; A61B 19/04
See application file for complete search history.

(56) References Cited

U.S. PATENT DOCUMENTS

| | | | | |
|---|---|---|---|---|
| 2,741,410 A * | 4/1956 | La Violette | ............ | A61B 42/00 223/111 |
| 3,695,493 A * | 10/1972 | Karr | ............... | A47G 25/904 223/111 |
| 4,002,276 A * | 1/1977 | Poncy | ............... | A61B 42/50 223/111 |
| 4,889,266 A * | 12/1989 | Wight | ............... | A61B 42/50 223/111 |
| 4,909,413 A * | 3/1990 | McCutcheon | ....... | A47G 25/904 221/1 |
| 4,915,272 A * | 4/1990 | Vlock | ............... | A47G 25/904 206/278 |
| 5,058,785 A * | 10/1991 | Rich | ............... | A61B 42/40 223/111 |
| 5,078,308 A * | 1/1992 | Sullivan | ............... | A47G 25/904 206/278 |
| 5,868,290 A * | 2/1999 | Green, Sr. | ............ | A47G 25/904 223/111 |
| D440,740 S | 4/2001 | Anctil | | |
| 7,377,410 B1 * | 5/2008 | Webb | ............... | A47G 25/904 223/111 |
| 7,805,772 B2 | 10/2010 | Williams | | |
| 9,668,601 B1 * | 6/2017 | Rogers | ............... | A61B 42/50 |
| 10,912,405 B1 * | 2/2021 | McCarthy | ............ | A47G 25/904 |
| 2002/0050499 A1 * | 5/2002 | Binder | ............... | A61B 42/30 223/111 |
| 2003/0094468 A1 * | 5/2003 | Sinai | ............... | A61B 42/50 223/111 |
| 2021/0085412 A1 * | 3/2021 | Moghadam | ............ | A61B 42/50 |

* cited by examiner

*Primary Examiner* — Nathan E Durham

(57) ABSTRACT

A latex glove inflation assembly includes a housing that is fluidly coupled to a vacuum source for purging the housing of air. The housing has a pair of glove apertures extending into an interior of the housing. A plurality of engagements is each distributed around a respective one of the glove apertures. Each of the engagements engages a wrist opening on a respective pair of latex gloves when the engagements are turned on. The latex gloves are inflated when the housing is purged of air thereby facilitating a user to insert their hands into the gloves. Each of the engagements releases the latex gloves when the engagements are turned off. A release is coupled to the housing and the release facilitates air to fill the housing when the release is turned on thereby facilitating each of the latex gloves to deflate around the user's hands.

14 Claims, 5 Drawing Sheets

LATEX GLOVE INFLATION ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to inflation devices and more particularly pertains to a new inflation device for inflating latex gloves to enhance wearing the latex gloves.

(2) Description of Related Art Including Information Disclosed Under 37 CFR 1.97 and 1.98

The prior art relates to inflation devices.

BRIEF SUMMARY OF THE INVENTION

An embodiment of the disclosure meets the needs presented above by generally comprising a housing that is fluidly coupled to a vacuum source for purging the housing of air. The housing has a pair of glove apertures extending into an interior of the housing. A plurality of engagements is each distributed around a respective one of the glove apertures. Each of the engagements engages a wrist opening on a respective pair of latex gloves when the engagements are turned on. The latex gloves are inflated when the housing is purged of air thereby facilitating a user to insert their hands into the gloves. each of the engagements releasing the latex gloves when the engagements are turned off. A release is coupled to the housing and the release facilitates air to fill the housing when the release is turned on thereby facilitating each of the latex gloves to deflate around the user's hands.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
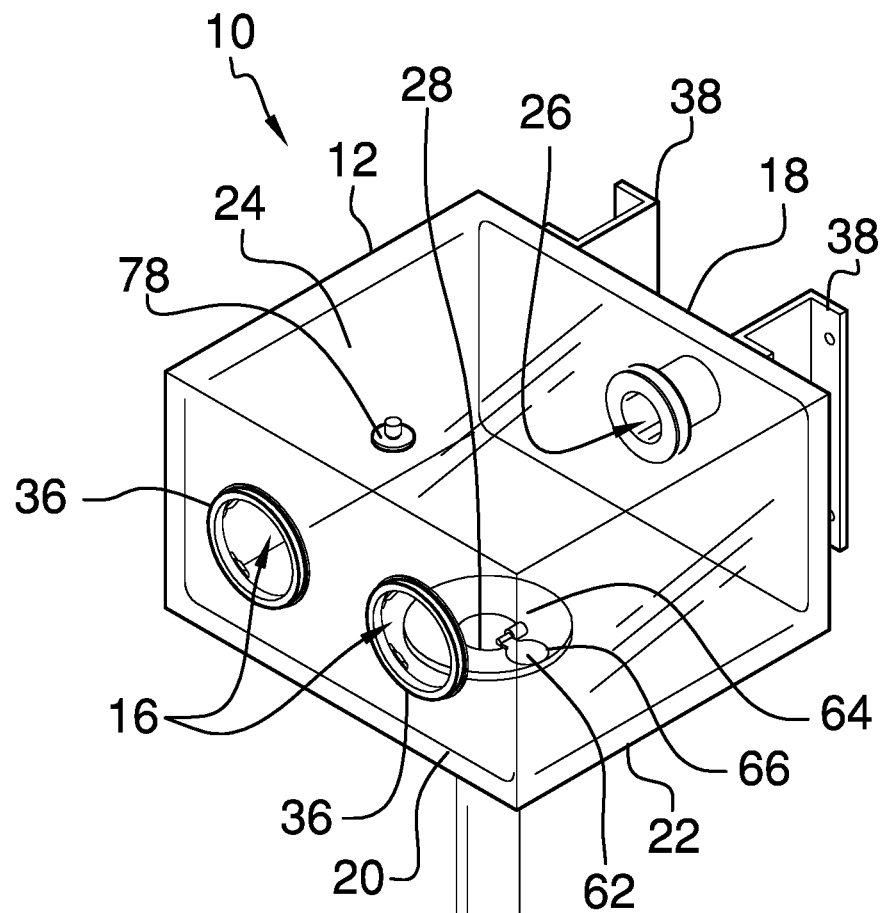
FIG. 1 is a perspective view of a latex glove inflation assembly according to an embodiment of the disclosure.
Figure 2:
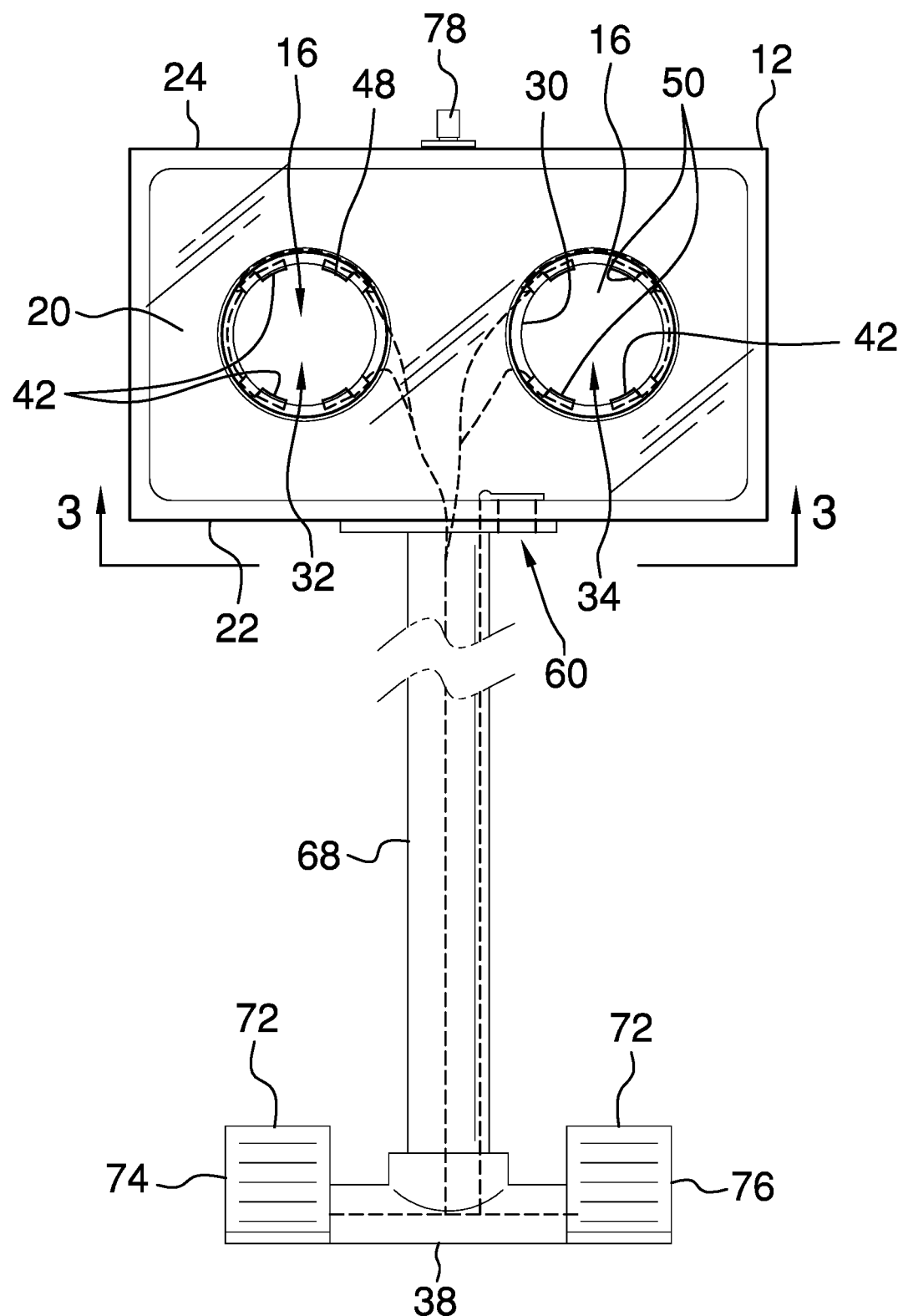
FIG. 2 is a front phantom view of an embodiment of the disclosure.
Figure 3:
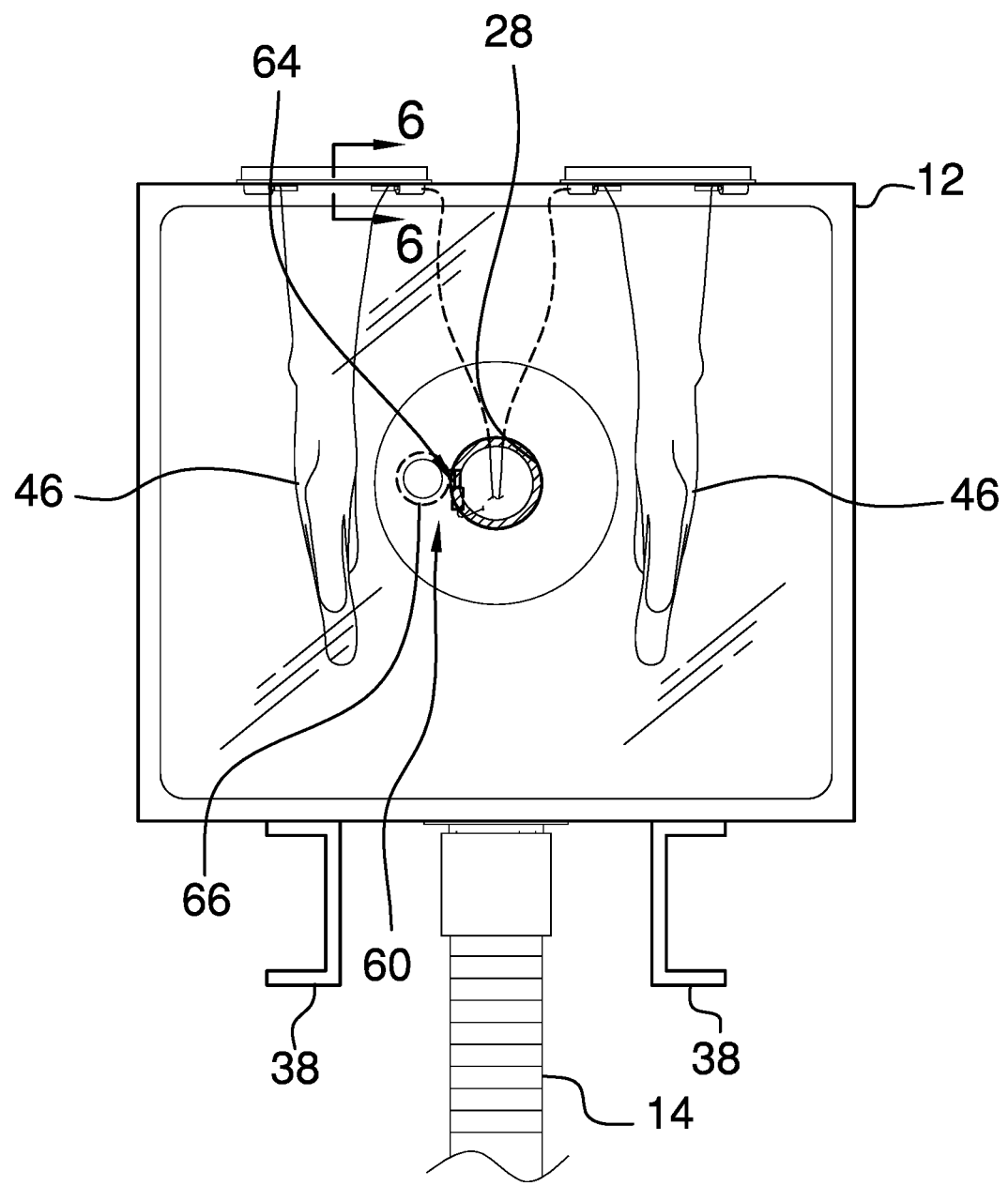
FIG. 3 is a top view of an embodiment of the disclosure.
Figure 4:
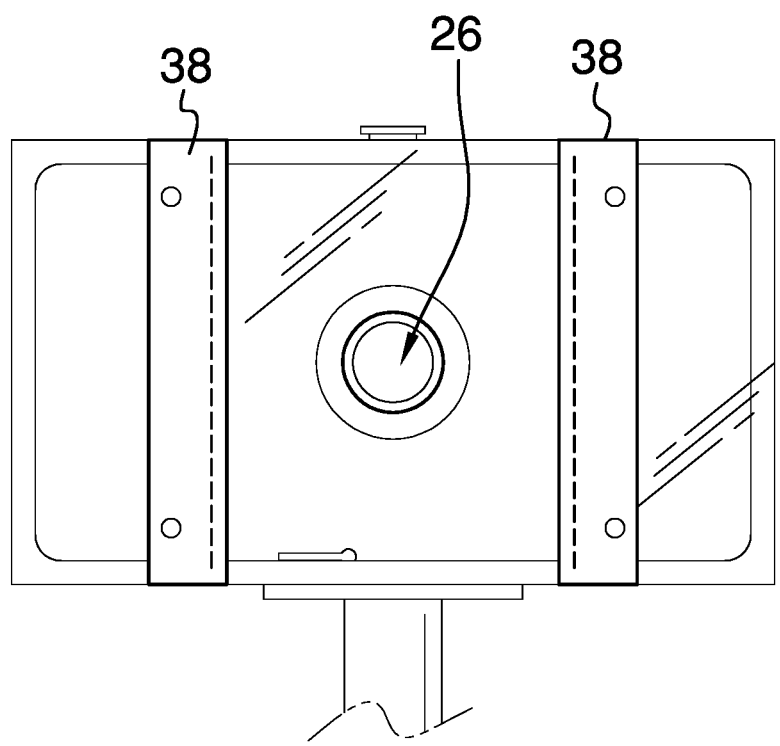
FIG. 4 is a back view of an embodiment of the disclosure.
Figure 5:
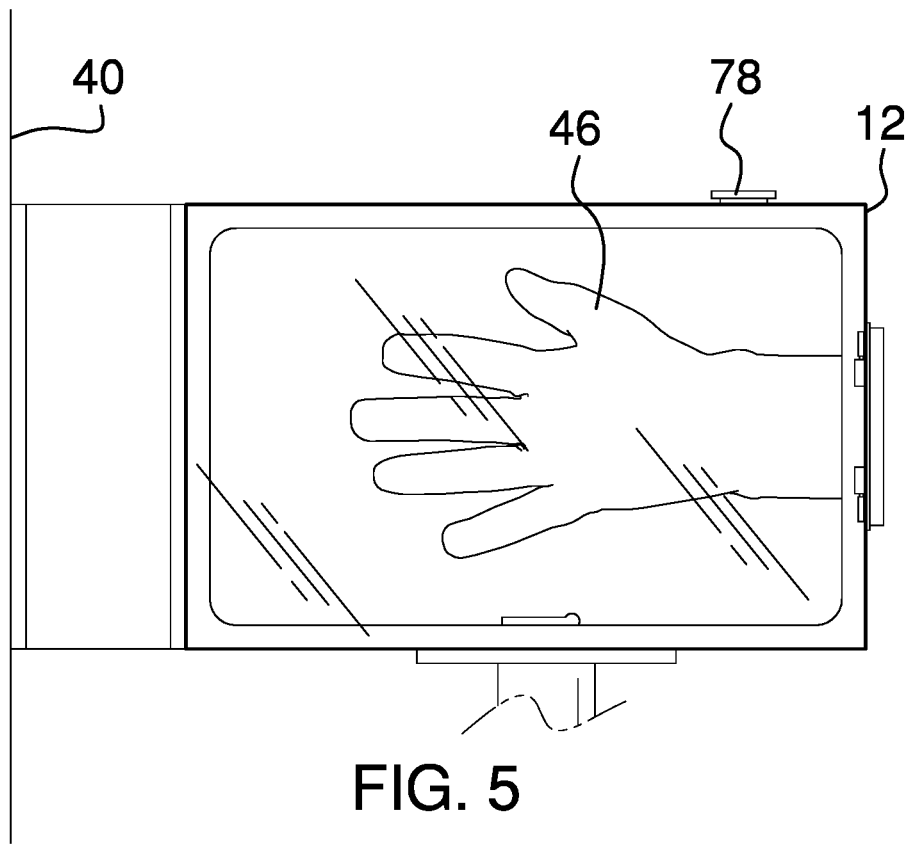
FIG. 5 is a left side view of an embodiment of the disclosure.
Figure 6:
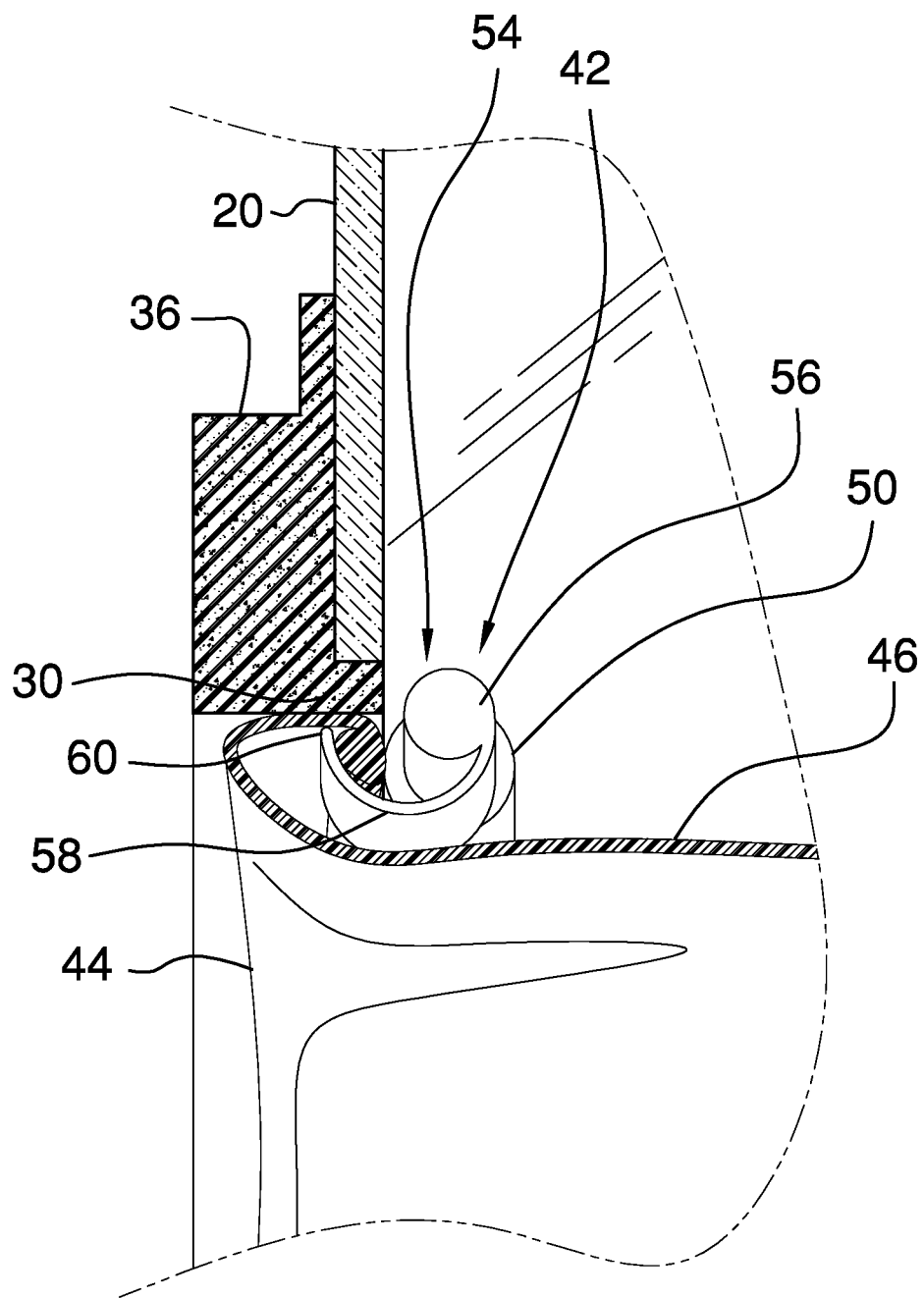
FIG. 6 is a cross sectional view taken along line 6-6 of FIG. 3 of an embodiment of the disclosure.

With reference now to the drawings, and in particular to FIGS. 1 through 6 thereof, a new inflation device embodying the principles and concepts of an embodiment of the disclosure and generally designated by the reference numeral 10 will be described.

As best illustrated in FIGS. 1 through 6, the latex glove inflation assembly 10 generally comprises a housing 12 that is fluidly coupled to a vacuum source 14 thereby facilitating the housing 12 to be purged of air. The vacuum source 14 may a vacuum system in a hospital and the housing 12 may be positioned in an operating room of the hospital. The housing 12 has a pair of glove apertures 16 that each extends into an interior of the housing 12. The housing 12 has a back wall 18, a front wall 20, a bottom wall 22 and a top wall 24. The housing 12 is comprised of an air impermeable and translucent material.

The back wall 18 has a suction aperture 26 extending into an interior of the housing 12 and the bottom wall 22 has a release aperture 28 extending into the interior of the housing 12. Each of the glove apertures 16 extends into the interior of the housing 12 and each of the glove apertures 16 has a bounding edge 30. The pair of glove apertures 16 includes a first glove aperture 32 and a second glove aperture 34. The suction aperture 26 is fluidly coupled to the vacuum source 14.

A pair of grommets 36 is provided and each of the grommets 36 forms a closed loop. Each of the grommets 36 is coupled to the bounding edge 30 of a respective one of the glove apertures 16. A pair of brackets 38 is each coupled to and extends away from the back wall 18 of the housing 12. Each of the brackets 38 is fastenable to a support surface 40 for retaining the housing 12 on the support surface 40. The support surface 40 may be a wall in the operating room or other vertical support surface. Additionally, the housing 12 may be positioned at a strategic height to facilitate a user to insert each of the user's hands into the glove apertures 16. The user may be a surgeon or other individual that has previously sterilized their hands.

A plurality of engagements 42 is provided and each of the engagements 42 is coupled to the housing 12. Each of the engagements 42 is distributed around a respective one of the glove apertures 16. Additionally, each of the engagements 42 engages a wrist opening 44 on a respective pair of latex gloves 46 when the engagements 42 are turned on. Moreover, the latex gloves 46 are positioned within the housing 12 when the engagements 42 engage the latex gloves 46. In this way each of the latex gloves 46 is inflated when the housing 12 is purged of air thereby facilitating the user to insert their hands into the gloves. Thus, the user can wear the latex gloves 46 without compromising the sterility of their hands. The latex gloves 46 may be surgical gloves of any conventional design.

Each of the engagements 42 releases the latex gloves 46 when the engagements 42 are turned off. The plurality of engagements 42 includes a set of first engagements 48 and a set of second engagements 50. Each of the first engagements 48 is distributed around the first glove aperture 32 and each of the second engagements 50 is distributed around the second glove aperture 34. Each of the engagements 42 comprises a clamp motor 52 that is coupled to an interior surface 54 of the front wall 20 of the housing 12. The clamp motor 52 is aligned with the bounding edge 30 of a respective one of the glove apertures 16, and the clamp motor 52 rotates in a first direction or a second direction. The clamp motor 52 may be an electric motor or the like.

Each of the engagements 42 includes a clamp 54 that has a shaft 56 and a finger 58 extending away from the shaft 56. The finger 58 has a distal end 60 with respect to the shaft 56 and the finger 58 is curved between the shaft 56 and the distal end 60. The shaft 56 is coupled to the clamp motor 52. The distal end 60 of the finger 58 is urged toward the bounding edge 30 of the respective glove aperture 16 when the clamp motor 52 rotates in the first direction. In this way the finger 58 compresses the latex glove 46 against the bounding edge 30. The finger 58 is urged away from the bounding edge 30 of the respective glove aperture 16 when the clamp motor 52 rotates in the second direction. In this way the finger 58 disengages from the latex glove 16 thereby facilitating the latex glove 16 to be removed from the housing 12.

A release 62 is coupled to the housing 12 and the release 62 facilitates air to fill the housing 12 when the release 62 is turned on. In this way each of the latex gloves 46 deflates around the user's hands. The release 62 comprises a release motor 64 that is coupled to the bottom wall 22 of the housing 12. The release motor 64 is rotatable in a first direction or a second direction. Additionally, the release motor 64 may comprise an electric motor or the like.

The release 62 includes a valve 66 that is coupled to the release motor 64. The valve 66 covers the release aperture 28 when the release motor 64 rotates in the first direction. Additionally, the valve 66 forms an air impermeable seal with the bottom wall 22 of the housing 12 when the valve 66 covers the release aperture 28. In this way the valve 66 retains the vacuum within the housing 12. The valve 66 is displaced from the release aperture 28 when the release motor 64 rotates in the second direction to facilitate air to fill the housing 12. A pole 68 is coupled to and extends downwardly from the bottom wall 22 of the housing 12 and the pole 68 has a distal end 70 with respect to the housing 12.

A pair of pedals 72 is provided and each of the pedals 72 is pivotally coupled to the distal end 70 of the pole 68 and each of the pedals 72 can be stepped on the by the user. Each of the pedals 72 is electrically coupled to respective ones of the engagements 42 and the release 62 for turning the engagements 42 and the release 62 on and off. Additionally, each of the pedals 72 is biased into a home position.

The pair of pedals 72 includes an engagement pedal 74 and a release pedal 76. The engagement pedal 74 is electrically coupled to the clamp motor 52 of each of the engagements 42 and the clamp motor 52 of each of the engagements 42 rotates in the first direction when the engagement pedal 74 is stepped on. Moreover, the clamp motor 52 of each of the engagements 42 rotates in the second direction when the clamp 54 pedal is not stepped on. The release pedal 76 is electrically coupled to the release motor 64 and the release motor 64 rotates in the second direction when the release pedal 76 is stepped on. The release motor 64 rotates in the first direction when the release pedal 76 is not stepped on. Each of the engagement pedal 74 and the release pedal 76 is electrically coupled to a power source, such as the electrical system of the hospital.

A safety valve 78 is coupled to the top wall 24 of the housing 12 and the safety valve 78 is in fluid communication with the interior of the housing 12. The safety valve 78 is in a normally closed condition. The safety valve 78 is urged into an open condition when air pressure within the housing 12 reaches dangerous levels. In this way the air pressure within the housing 12 is equalized with respect to ambient air. The safety valve 78 may be an air pressure relief valve 66 or the like.

In use, each of the latex gloves 46 is positioned in the respective glove aperture 16 and the wrist opening 44 of each of the latex gloves 46 is positioned in the engagements 42 around the respective glove aperture 16. The engagement pedal 74 is stepped on to facilitate the engagements 42 to engage the wrist opening 44 of the respective latex glove 46. The release pedal 76 is stepped on the close the valve 66, thereby facilitating the vacuum source 14 to depressurize the interior of the housing 12. In this way each of the latex gloves 46 is inflated thereby facilitating the user to insert their hands into each of the latex gloves 46. The release pedal 76 is released thereby facilitating the housing 12 to be pressurized. Thus, the latex gloves 46 deflate around the user's hands. In this way the user can put on the latex gloves 46 without compromising the sterility of the user's hands.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:
1. A latex glove inflation assembly being configured to inflate a pair of latex gloves thereby enhancing a user placing the latex gloves on their hands, said assembly comprising:
   a housing being fluidly coupled to a vacuum source wherein said housing is configured to he purged of air, said housing having a pair of glove apertures extending into an interior of said housing;
   a plurality of engagements, each of said engagements being coupled to said housing, each of said engagement being distributed around a respective one of said glove apertures, each of said engagements being configured for engaging a wrist opening on a respective pair of latex gloves when said engagements are turned on having the latex gloves being positioned within said housing wherein each of said latex gloves is configured to be inflated when said housing is purged of air thereby facilitating a user to insert their hands into said gloves, each of said engagements being configured for releasing the latex gloves when said engagements are turned off;
   a release being coupled to said housing, said release facilitating air to fill said housing when said release is turned on thereby facilitating each of the latex gloves to deflate around the user's hands;
   a pole being coupled to and extending downwardly from said housing; and
   a pair of pedals, each of said pedals being pivotally coupled to said pole wherein each of said pedals is configured to be stepped on the by the user, each of said pedals being electrically coupled to respective ones of said engagements and said release for turning said engagements and said release on and off, each of said pedals being biased into a home position.

2. The assembly according to claim 1, wherein said housing has a back wall, a front wall, a bottom wall and a top wall, said housing being comprised of an air impermeable material, said back wall having a suction aperture extending into an interior of said housing, said bottom wall having a release aperture extending into said interior of said housing, each of said glove apertures extending into interior of said housing, each of said glove apertures having a bounding edge, said pair of glove apertures including a first glove aperture and a second glove aperture, said suction aperture being fluidly coupled to the vacuum source.

3. The assembly according to claim 2, further comprising a pair of brackets, each of said brackets being coupled to and extending away from said back wall of said housing, each of said brackets being fastenable to a support surface for retaining said housing on the support surface.

4. The assembly according to claim 2, wherein said plurality of engagements including a set of first engagements and a set of second engagements, each of said first engagements being distributed around said first glove aperture, each of said second engagements being distributed around said second glove aperture.

5. The assembly according to claim 4, wherein each of said engagements comprises a clamp motor being coupled to an interior surface of said front wall of said housing, said clamp motor being aligned with said bounding edge of a respective one of said glove apertures, said clamp motor rotating in a first direction or a second direction.

6. The assembly according to claim 5, wherein each of said engagements includes a clamp having a shaft and a finger extending away from said shaft, said finger having a distal end with respect to said shaft, said finger being curved between said shaft and said distal end, said shaft being coupled to said clamp motor.

7. The assembly according to claim 6, wherein said distal end of said finger is urged toward said bounding edge of said respective glove aperture when said clamp motor rotates in said first direction wherein said finger is configured to compress the latex glove against said bounding edge.

8. The assembly according to claim 7, wherein said finger is urged away from said bounding edge of said respective glove aperture when said clamp motor rotates in said second direction wherein said finger is configured to disengage from the latex glove thereby facilitating the latex glove to be removed from said housing.

9. The assembly according to claim 5, wherein said pair of pedals includes an engagement pedal, said engagement pedal being electrically coupled to each of said clamp motors, each of said clamp motors rotating in said first direction when said engagement pedal is stepped on, each of said clamp motors rotating in said second direction when said clamp pedal is not stepped on.

10. The assembly according to claim 2, wherein said release comprises a release motor being coupled to said bottom wall of said housing, said release motor being rotatable in a first direction or a second direction.

11. The assembly according to claim 10, wherein said release comprises a valve being coupled to said release motor, said valve covering said release aperture when said release motor rotates in said first direction, said valve forming an air impermeable seal with said bottom wall of said housing when said valve covers said release aperture wherein said valve is configured to retain the vacuum within said housing, said valve being displaced from said release aperture when said release motor rotates in said second direction wherein said release aperture is configured to facilitate air to fill said housing.

12. The assembly according to claim 10, wherein said pair of pedals includes a release pedal, said release pedal being electrically coupled to said release motor, said release motor rotating in said second direction when said release pedal is stepped on, said release motor rotating in said first direction when said release pedal is not stepped on, each of said engagement pedal and said release pedal being electrically coupled to a power source.

13. The assembly according to claim 2, further comprising a safety valve being coupled to said top wall of said housing, said safety valve being in fluid communication with said interior of said housing, said safety valve being in a normally closed condition, said safety valve being urged into an open condition when air pressure within said housing reaches dangerous levels for equalizing air pressure within said housing with respect to ambient air.

14. A latex glove inflation assembly being configured to inflate a pair of latex gloves thereby enhancing a user placing the latex gloves on their hands, said assembly comprising:
   a housing being fluidly coupled to a vacuum source wherein said housing is configured to be purged of air, said housing having a pair of glove apertures extending into an interior of said housing, said housing having a back wall, a front wall, a bottom wall and a top wall, said housing being comprised of an air impermeable material, said back wall having a suction aperture extending into an interior of said housing, said bottom wall having a release aperture extending into said interior of said housing, each of said glove apertures extending into said interior of said housing, each of said glove apertures having a bounding edge, said pair of glove apertures including a first glove aperture and a second glove aperture, said suction aperture being fluidly coupled to the vacuum source;

a pair of grommets, each of said grommets forming a closed loop, each of said grommets being coupled to said bounding edge of a respective one of said glove apertures;

a pair of brackets, each of said brackets being coupled to and extending away from said back wall of said housing, each of said brackets being fastenable to a support surface for retaining said housing on the support surface;

a plurality of engagements, each of said engagements being coupled to said housing, each of said engagement being distributed around a respective one of said glove apertures, each of said engagements being configured for engaging a wrist opening on a respective pair of latex gloves when said engagements are turned on having the latex gloves being positioned within said housing wherein each of said latex gloves is configured to be inflated when said housing is purged of air thereby facilitating a user to insert their hands into said gloves, each of said engagements being configured for releasing the latex gloves when said engagements are turned off, said plurality of engagements including a set of first engagements and a set of second engagements, each of said first engagements being distributed around said first glove aperture, each of said second engagements being distributed around said second glove aperture, each of said engagements comprising:
  a clamp motor being coupled to an interior surface of said front wall of said housing, said clamp motor being aligned with said bounding edge of a respective one of said glove apertures, said clamp motor rotating in a first direction or a second direction; and
  a clamp having a shaft and a finger extending away from said shaft, said finger having a distal end with respect to said shaft, said finger being curved between said shall and said distal end, said shaft being coupled to said clamp motor, said distal end of said finger being urged toward said bounding edge of said respective glove aperture when said clamp motor rotates in said first direction wherein said finger is configured to compress the latex glove against said bounding edge, said finger being urged away from said bounding edge of said respective glove aperture when said clamp motor rotates in said second direction wherein said finger is configured to disengage from the latex glove thereby facilitating the latex glove to be removed from said housing;

a release being coupled to said housing, said release facilitating air to fill said housing when said release is turned on thereby facilitating each of the latex gloves to deflate around the user's hands, said release comprising:
  a release motor being coupled to said bottom wall of said housing, said release motor being rotatable in a first direction or a second direction; and
  a valve being coupled to said release motor, said valve covering said release aperture when said release motor rotates in said first direction, said valve forming an air impermeable seal with said bottom wall of said housing when said valve covers said release aperture wherein said valve is configured to retain the vacuum within said housing, said valve being displaced from said release aperture when said release motor rotates in said second direction wherein said release aperture is configured to facilitate air to fill said housing;

a pole being coupled to and extending downwardly from said bottom wall of said housing, said pole having a distal end with respect to said housing;

a pair of pedals, each of said pedals being pivotally coupled to said distal end of said pole wherein each of said pedals is configured to be stepped on the by the user, each of said pedals being electrically coupled to respective ones of said engagements and said release for turning said engagements and said release on and off, each of said pedals being biased into a home position, said pair of pedals including an engagement pedal and a release pedal, said engagement pedal being electrically coupled to each of said clamp motors, each of said clamp motors rotating in said first direction when said engagement pedal is stepped on, each of said clamp motors rotating in said second direction when said clamp pedal is not stepped on, said release pedal being electrically coupled to said release motor, said release motor rotating in said second direction when said release pedal is stepped on, said release motor rotating in said first direction when said release pedal is not stepped on, each of said engagement pedal and said release pedal being electrically coupled to a power source; and a safety valve being coupled to said top wall of said housing, said safety valve being in fluid communication with said interior of said housing, said safety valve being in a normally closed condition, said safety valve being urged into an open condition when air pressure within said housing reaches dangerous levels for equalizing air pressure within said housing with respect to ambient air.

* * * * *